United States Patent [19]

Gianturco

[11] 4,445,896
[45] May 1, 1984

[54] CATHETER PLUG

[75] Inventor: Cesare Gianturco, Champaign, Ill.

[73] Assignee: Cook, Inc., Bloomington, Ind.

[21] Appl. No.: 359,218

[22] Filed: Mar. 18, 1982

[51] Int. Cl.³ ............................................. A61M 25/00
[52] U.S. Cl. .................................... 604/238; 604/244; 604/283; 604/415; 604/88
[58] Field of Search ...................... 604/86, 87, 88, 238, 604/244, 256, 280, 283, 415, 905

[56] References Cited

U.S. PATENT DOCUMENTS

| | | | |
|---|---|---|---|
| 3,081,029 | 3/1963 | Gauslaa | 604/415 X |
| 3,682,315 | 8/1972 | Haller | 604/415 X |
| 4,254,773 | 3/1981 | Waldbillig | 604/283 |
| 4,360,024 | 11/1982 | Wallace | 604/283 X |

Primary Examiner—Stephen C. Pellegrino
Attorney, Agent, or Firm—Woodard, Weikart, Emhardt & Naughton

[57] ABSTRACT

A catheter plug for sealing the proximal end of a parenterally placed catheter and permitting repeated small volume injections and delivery of parenteral fluids without disturbing the sterility of the catheter. The catheter plug has a compression chamber for applying compression to a self-sealing elastometric septum thereby enhancing the septum's self-sealing characteristics. Compression force is applied to the septum by screw movement between oppositely threaded male and female couplers. The catheter plug is particularly useful in situations where pressures higher than arterial pressures are encountered or where it is desirable to leave the catheter indwelling for long periods of time.

14 Claims, 2 Drawing Figures

CATHETER PLUG

BACKGROUND OF THE INVENTION

The present invention relates to a self-sealing plug for a catheter and a method for constructing the same.

Frequently in the field of medical practice, indwelling catheters are employed for large volume injections or removal of parenteral fluids. Typical examples of such uses are intravenous feeding and use of artificial kidneys. In such situations, it is very often necessary to administer small volume injections of drugs or samplings of parenteral fluids. In order to avoid the pain and discomfort accompanying direct insertion of hypodermic needles, injection ports are frequently provided in the catheter tubing or attached thereto by an adapter or other connecting device. The injection port is constructed so that injections can be made without affecting the sterility of the catheter or allowing parenteral fluids to enter and fill the catheter from the distal end and escape through the proximal end. Self-sealing injection ports which accomplish this purpose have been known in the art for some time. Several examples of self-sealing injection ports are disclosed in U.S. Pat. Nos. 3,898,988; 3,990,445; 4,187,149; 4,111,326; and 4,219,912. Other disclosures of possible relevance are U.S. Pat. Nos. 3,951,145 and 4,046,145.

In certain medical applications however, the injection port experiences higher than normal pressures. For example, during chemotherapy treatments, an infusion pump is used to slowly infuse cancer-treating drugs in the area of a tumor. Back pressures considerably higher than arterial pressures are typically developed by the pump inside the catheter. A manifold system is employed to permit injections of other drugs directly into the catheter without having to dilute such drugs by injection into the slowly infused chemotherapy liquids or necessitate the pain and discomfort of repeated hypodermic needle injections through the skin.

Especially in the field of chemotherapy, drug injections at a slow rate over a relatively long period of time must be administered for effective medical treatment. In such situations, it is highly desirable to allow the catheter to the left indwelling between chemotherapy treatments, thereby eliminating the need to reinsert and remove the catheter during each successive treatment. One problem which can be encountered when a catheter is left indwelling for relatively long periods is bacteria entering the distal end of the catheter and causing infection. It is therefore necessary to provide a seal which will maintain the sterility of the catheter and yet be easily removable. Such devices are well known in the art. However, it is also highly desirable to be able to administer small volume injections directly into the catheter or to take samplings of parenteral fluids needed between treatments directly from the catheter, thus avoiding the pain and discomfort accompanying direct insertion of hypodermic needles.

Previous devices for self-sealing injection ports have not been completely satisfactory where high back pressures are developed, or where catheters are left indwelling for a long period of time. The present invention relates to a device and method of constructing a device which provides improved self-sealing capabilities for injection ports used for small volume parenteral sampling and delivery systems and which is designed for ease of assembly during manufacture and yet it also relatively cheap to manufacture.

Accordingly, it is an object of the present invention to provide an improved self-sealing injection port for small volume parenteral sampling and delivery systems which permits a catheter to be kept indwelling for long periods of time in sterile condition and which is highly leak resistant under repeated use.

It is a further object of the present invention to provide an improved self-sealing injection port for small volume parenteral sampling and delivery systems which is useful for applications where high back pressures might be encountered, such as in a manifold system which is coupled to an infusion pump during chemotherapy treatments.

It is a still further object of the present invention to provide an improved self-sealing injection port used for small volume parenteral sampling and delivery systems which is easy to assemble during manufacture.

It is a still further object of the present invention to provide an improved self-sealing injection port used for small volume parenteral and delivery systems which is relatively cheap to manufacture and use.

These and other objects and advantages of the present invention will become more apparent in the following figures and detailed description.

SUMMARY OF THE INVENTION

One embodiment of the invention includes a connector having two ends and a passage therethrough, the first end being suitably adapted to couple to a catheter and the second end being adapted for male-female coupling. A cap having an injection port therethrough is coupled at one end in male-female fashion with the second end of the connector. A septum means suitably adapted for piercing with a pointed instrument and spatially compressible is frictionally held within a compression chamber between the connector and the cap.

DESCRIPTION OF THE PREFERRED EMBODIMENT

Figure 1:
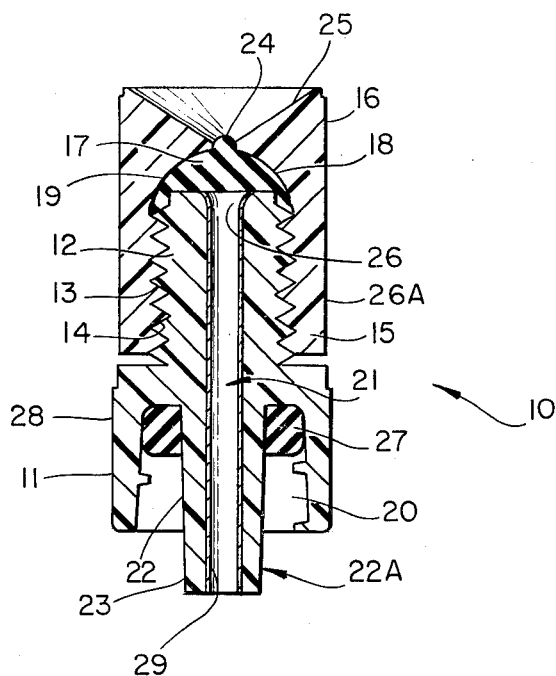
FIG. 1 is an enlarged sectional view taken axially of the preferred embodiment of the catheter plug of the present invention after assembly.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, a self-sealing catheter plug 10 includes a connector 11 having a male end 12 with threads 13 for male-female coupling with complementary threaded inner walls 14 of female end 15 of cap 16. The cap and connector may be formed for example of an acetel such as Calcon, a product of Celanese, Inc. Adhesive, such as epoxy, is placed on threads 13 when the plug 10 is assembled so that septum 17 is held in a compressed position inside a compression chamber 18 which is defined by the concave inner surface 19 of female end 15 and the male end 12 of connector 11. The concave shape serves to permit septum 17 to spatially compress in a manner more fully described herein below. The other end of connector 11 has a female portion 20 of a Luer lock which connects to the male portion of the Luer lock on the end of a parenterally placed catheter (not shown) as is well known in the prior art. Axial passage 21 extends longitudinally through connector 11 and serves to guide the hypodermic needle into the catheter after piercing through septum 17. The walls 22 surrounding axial passage 21 form a tubular coupler 22A which extends longitudinally through and is collared by female Luer lock portion 20. The distal end 23 of the tubular coupler extends out of the collar, allowing the distal end 23 to be visible during coupling. A doughnut shaped compressionable seal 27 is received around tubular coupler 22A and is compressed into the annular recess of the female Luer lock portion 20 during coupling.

The function of the self-sealing catheter plug 10 is to keep the end of the catheter sterile by sealing the end of the catheter and to permit penetration by a hypodermic needle through the latex rubber septum 17 for sampling or for small volume injections. Cap 16 is of generally external cylindrical shape and has an injection port 24 which has a diameter slightly larger than the diameter of a 21 or 22 gauge hypodermic needle. A recess 25 includes an outwardly tapering frustoconical wall which extends from injection port 24 and joins with the cylindrical outer surface 26 of the cap 16. The recess 25 serves to aid the placement of a hypodermic needle into injection port 24 whereupon the hypodermic needle pierces septum 17 and projects into axial passage 21 which thereafter guides the hypodermic needle into the proximal end of the catheter. Since the latex rubber septum 17 is spatially compressed inside compressional chamber 18 during assembly, it will close tightly and seal injection port 24 when the hypodermic needle is removed. Axial passage 21 has a larger diameter than injection port 24 which allows some error in the direction of entry of the hypodermic needle to be tolerated without the needle missing axial passage 21. Axial passage 21 has a slight taper 26 at its proximal end which slightly increases the diameter of axial passage 21 at its proximal end, further aiding the correct insertion of the hypodermic needle and eliminating any sharp edges which would otherwise tend to pierce into septum 17.

Figure 2:
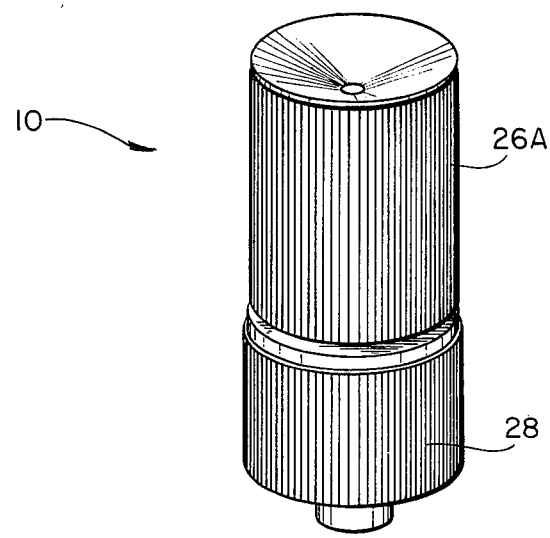
FIG. 2 is an enlarged perspective view of the structure of FIG. 1.

Connector 11 and cap 16 are preferably made from plastic such as the above mentioned acetel except that axial passage 21 of connector 11 has a relatively thin metallic wall 29 in order to prevent the hypodermic needle from piercing into connector 11 as it is guided through axial passage 21. This metallic wall may be formed, for example, of cannula material stainless steel about 0.004 inches thick. Septum 17 and seal 27 are preferably made of latex rubber. Septum 17 is suitably shaped so that it readily occupies the available volume of compression chamber 18 during compression. Referring to FIG. 2, the cylindrical outer surface 26A of the cap has a slightly smaller diameter than the cylindrical outer surface 28 of the connector and both cylindrical outer surfaces 26A and 28 are serrated to permit screw compression to be easily applied during assembly.

From the foregoing, it should be apparent that a specific and unique feature of the present invention is the compression chamber 18 in which septum 17 is placed. The two openings into compression chamber 18 have minimal cross-sectional areas when compared to the total surface area of the compression chamber and the shape of the compression chamber is concave adjacent port 24. As a result of this construction, septum 17 receives a compression force which acts axially, radially and obliquely. This spatial compression occurs over practically its entire outer surface and has been found to enhance the self-sealing characteristics of the septum material. Thus it has been found that one preferred embodiment of the invention with a latex septum withstood pressures up to 100 psi after having been punctured several times without leaking.

Still another advantage of the invention is that the screw compression design is simple to assemble, requiring a minimum of separate parts and allowing a considerable amount of compressive force to be attained with minimal effort of assembly.

Although only one embodiment of the present invention has been described above, it should be appreciated that many modifications can be made without departing from the spirit and scope of the present invention. Finally, it should be noted that while the invention described in the preferred embodiment is used to seal an indwelling catheter, it is by no means limited to such application. Suitable applications for the above described invention include any situation which requires introduction or removal of fluids or gases from a sealed enclosure without breaking the sterility of the enclosure.

What is claimed is:
1. A self-sealing catheter plug comprising:
 (a) connector means having an end adapted to couple to a catheter and another end adapted for male-female coupling, said connector means having a passage therethrough;
 (b) cap means having an end adapted for male-female coupling with the connector means at said another end, said cap means having an injection port therethrough aligned with said passage;
 (c) septum means for sealing the port and adapted for piercing with a pointed instrument said septum means frictionally held and spatially compressed within a compression chamber between said connector means and said cap means.
2. The catheter plug of claim 1, wherein said another end of the connector means is male and said end of the cap means is female, said cap means including an inner concave surface, and said compression chamber being defined by said concave surface in said cap means and the end of said connector.
3. The catheter plug of claim 2 wherein said connector means and cap means have complementary threaded walls with adhesive therebetween.
4. The catheter plug of claim 3 wherein said connector means catheter coupling end is a Luer lock and said cap means is recessed frustoconically from said port outwardly.
5. The catheter plug of claim 4 wherein said septum means is made of latex and said connector means and said cap means are plastic except that said connector means passage has a thin metallic wall.
6. The catheter plug of claim 5 wherein the external surfaces of said connector means and said cap means are generally cylindrical shaped and said connector means and said cap means have longitudinal serrations upon said surfaces, said connector means cylindrical surface having a slightly larger diameter than said cap means cylindrical surface.

7. A parenteral fluid sampling and delivery system for attachment to a catheter, comprising:
   (a) compressor means for applying spatial compression to a volume occupying body;
   (b) spatially compressed septum means frictionally held inside said compressor means, said compressor means having an opening therethrough suitably formed for guiding a piercing instrument through the septum and the compressor means.

8. The device of claim 7 wherein the compressor means includes first and second coupling members suitably adapted for male-female coupling with each other, said second coupling member defining an inner surface which is concave said septum means being frictionally held within a compression chamber defined by the concave inner surface of the second coupling member and the first coupling member, said compressor means opening extending longitudinally through the first and second coupling members, said opening being aligned through said members to allow placement of a piercing instrument therethrough.

9. The device of claim 8 wherein the first coupling member is male and the second coupling member is female, said first coupling member having an end adapted to couple with a catheter tube and said male and female members have complementary threaded walls with adhesive therebetween.

10. The device of claim 9 wherein the second end of said first coupling member is a Luer lock, the opening through said male coupling member tapers outwardly towards said female coupling member at the proximal end, and the opening through said female coupling member has a first portion which tapers frustoconically outwards towards the distal end of said female coupling member.

11. The device of claim 10 wherein said septum is made of latex and said male coupling member and said female coupling member are plastic, except that the male coupling member has a thin metal coating at said opening.

12. The device of claim 11 wherein said first and second coupling members have generally cylindrical shaped external surfaces with longitudinal serrations thereon.

13. A method for constructing small volume sampling and delivery systems suitable for connecting to a parenterally placed catheter comprising:
   (a) providing a catheter plug having a connector means and a cap means, said connector and cap means having aligned passages therethrough and suitably formed for male-female coupling with each other at one end, and said connector having a second end adapted to couple with a catheter;
   (b) inserting a self-sealing spatially compressible septum into the female coupling end;
   (c) coupling said connector means with the cap means, so as to spatially compress the septum therebetween and seal said connector means and cap means aligned passages at their one end;
   (d) locking the connector means and the cap means into their coupled positions so as to maintain spatial compression upon the septum.

14. The method of claim 13 wherein said coupling step is accomplished by screwing the male coupling end into the female coupling end until suitable compression of the septum is achieved, and said locking step comprises applying adhesive to the outer surface of the male screw coupling member prior to coupling and allowing the adhesive to dry after said coupling step is accomplished.

* * * * *